United States Patent
Pain et al.

(10) Patent No.: US 12,201,543 B2
(45) Date of Patent: Jan. 21, 2025

(54) ENDOSCOPIC GASTRIC PLICATION DEVICE

(71) Applicant: ENDOPLY, Rillieux-la-Pape (FR)

(72) Inventors: Bernard Pain, Monistrol sur Loire (FR); Jérôme Dargent, Lyons (FR)

(73) Assignee: ENDOPLY, Rillieux-la-Pape (FR)

( * ) Notice: Subject to any disclaimer, the term of this patent is extended or adjusted under 35 U.S.C. 154(b) by 0 days.

(21) Appl. No.: 18/727,590

(22) PCT Filed: Oct. 18, 2022

(86) PCT No.: PCT/FR2022/051964
§ 371 (c)(1),
(2) Date: Jul. 9, 2024

(87) PCT Pub. No.: WO2023/135370
PCT Pub. Date: Jul. 20, 2023

(65) Prior Publication Data
US 2024/0415681 A1    Dec. 19, 2024

(30) Foreign Application Priority Data

Jan. 12, 2022   (FR) ........................ 2200220

(51) Int. Cl.
*A61F 5/00* (2006.01)
*A61B 17/10* (2006.01)
(Continued)

(52) U.S. Cl.
CPC ............ *A61F 5/0086* (2013.01); *A61B 17/10* (2013.01); *A61B 17/1285* (2013.01);
(Continued)

(58) Field of Classification Search
CPC ...... A61F 5/0086; A61F 5/0089; A61B 17/10; A61B 17/1285; A61B 2017/00296; A61B 2017/06076; A61B 2017/306
See application file for complete search history.

(56) References Cited

U.S. PATENT DOCUMENTS

| | | | | |
|---|---|---|---|---|
| 5,769,857 A | * | 6/1998 | Reztzov | A61B 17/1285 606/151 |
| 2010/0137887 A1 | * | 6/2010 | Crockett | A61B 17/29 607/116 |

(Continued)

FOREIGN PATENT DOCUMENTS

EP    2189120 A1   5/2010

Primary Examiner — Richard G Louis
(74) Attorney, Agent, or Firm — FORGE IP, PLLC

(57) ABSTRACT

An endoscopic gastric plication device includes an assembly able to co-operate with a handle provided with a control mechanism for actuating the assembly for placing and securing a staple around a fold in a stomach wall. The device includes: a mechanism for gripping/pulling a portion of a stomach wall arranged at the end of a manipulation rod adapted to be connected to the control mechanism, which mechanism is capable of being actuated by the control mechanism so as to grip the stomach wall and pull it to form a fold; a mechanism for guiding a staple around the fold in the stomach wall; at least one staple and a mechanism for pushing the staple into the guide mechanism, the staple being designed to pass through and form a loop around the fold while being guided by the guide mechanism; and a mechanism for pulling the looped end of the staple.

11 Claims, 8 Drawing Sheets

(51) Int. Cl.
*A61B 17/128* (2006.01)
*A61B 17/00* (2006.01)
*A61B 17/06* (2006.01)
*A61B 17/30* (2006.01)

(52) U.S. Cl.
CPC .. *A61F 5/0089* (2013.01); *A61B 2017/00296* (2013.01); *A61B 2017/06076* (2013.01); *A61B 2017/306* (2013.01)

(56) References Cited

U.S. PATENT DOCUMENTS

| | | | |
|---|---|---|---|
| 2012/0330356 A1* | 12/2012 | Rosenberg | A61B 17/068 606/232 |
| 2013/0153642 A1 | 6/2013 | Felder et al. | |
| 2013/0338680 A1 | 12/2013 | Harris et al. | |
| 2015/0126983 A1 | 5/2015 | Alvarado et al. | |

* cited by examiner

ENDOSCOPIC GASTRIC PLICATION DEVICE

FIELD OF THE INVENTION

The present invention relates to the technical field of surgical devices used for the treatment of obesity, and more particularly relates to an endoscopic gastric plication device.

PRIOR ART

In the field of surgical devices used for the treatment of obesity, document US 2015 0126983 is known; it describes an endoscopic gastric plication device comprising an assembly which is capable of cooperating with a handle secured to control means.

The control means are designed to actuate the assembly in order to position and secure a length of suture around a fold formed in a gastric wall, with a view to creating a restriction of the fundus and the antrum of the stomach.

In the prior art, a helical needle is intended to be anchored in the stomach wall and to be pulled backwards in order to form a fold in the gastric wall.

Next, a needle through with the length of suture passes will make a stitch across the fold. Making two stitches which are spaced apart and connected together means that, after pulling the suture, said two stitches can be brought together in order to fold the gastric wall further and thereby reduce its volume.

The disadvantage with that type of device, apart from its complexity and its cost, is in the first place the use of a length of suture which could potentially cause a serious or minor mucosal and/or serosal tear, in particular in the long term. Thus, the durability of a suture is limited.

The effectiveness with using the helical needle to form the first fold cannot be guaranteed and may also cause a mucosal and/or serosal tear, but in particular, the helical needle often remains stuck in the tissues and causes a hemorrhage, which interferes endoscopic viewing.

The operation with that type of device is also complex and lengthy because two substantially parallel lines have to be traced in the stomach, which have to act as a guide for the positioning of the stitches, which then have to be tightened in the manner of shoelaces in order to close and restrict a portion of the stomach. What is more, the impermeability of the restricted portion of the stomach is not optimal.

In general, devices employing a length of suture considerably extend the duration of the surgical intervention. In fact, for each stitch, it is necessary to prepare and provide the suture, introduce it into the endoscope, position it at the end of the endoscope, grasp the gastric wall with a separate instrument, make a loop in the suture, lock the suture after applying a tension. All of these operations are carried out from outside by an assistant. Finally, the suture has to be cut and the device removed.

The foregoing shows that the succession of these manipulations on a suture are complex, lengthy and tedious.

DISCLOSURE OF THE INVENTION

One of the aims of the invention is therefore to overcome the disadvantages of the prior art by proposing an endoscopic gastric plication device which is simple in design and which can be used to carry out the surgical intervention in a manner which is less risky for the stomach wall, and more repeatable.

To this end, an endoscopic gastric plication device has been developed which conforms to that of the prior art in that it comprises an assembly which is capable of cooperating with a handle secured to control means in order to actuate the assembly for positioning and fixing a staple around a fold formed in a gastric wall.

To this end, the assembly comprises means for grasping/pulling a portion of the gastric wall, arranged at the end of a manipulating shaft intended to be connected to the control means and which can be actuated in order to come into engagement with the gastric wall and pull on it in order to form the fold.

In accordance with the invention, the device comprises:
  means for guiding the staple around the fold of the gastric wall;
  at least one staple, and means for pushing said staple in the guiding means, that staple being intended to come to be passed through and make a loop around the fold, guided by the guiding means.

In this manner, the device in accordance with the invention can be used to carry out a surgical gastric plication operation endoscopically while being capable of guiding a staple in an optimal and repeatable manner, and to securely fix it.

Thus, the operation is carried out by positioning a plurality of staples in succession, for example in a line in order to reduce the volume of the stomach. The fold or folds formed are closed at the outer wall of the stomach, with one or more staples positioned inside it. The volume of the stomach can be reduced without problems as regards impermeability. The operation only takes a few seconds for each staple, while in the prior art, the operation takes a few minutes for each stitch.

The grasping/pulling means are of any appropriate type, and are provided, for example, in the form of a helical needle extending in the extension of the manipulating shaft and which is intended to be anchored in the stomach wall by rotation. In accordance with another embodiment, the grasping/pulling means are in the form of a vacuum system.

In accordance with a preferred embodiment, and in order to avoid the risks of hemorrhages, the grasping/pulling means are in the form of a clamp which can be actuated in order to come to clamp and pull on a portion of the internal wall of the stomach with a view to forming a fold.

In accordance with a preferred embodiment, the guiding means comprise a guiding tube opening onto two jaws having sections in the form of a trough or channel for passing the staple through and guiding it. The jaws are capable of moving, for example in the manner of a clamp and by the action of the control means, from a closed guiding position in which the jaws clamp the fold of the gastric wall, to an open position for releasing the staple.

In this configuration, one of the jaws of the guiding means is fixed, for example, while the other jaw is articulated, for example by means of a cable disposed along the guiding tube.

The staple may be of any appropriate type, in particular long and extended, and in a preferred embodiment, the staple comprises an annular base from which a notched shaft extends which is intended to form a loop after having pierced and passed through the wall of the stomach, and to come to be inserted into and be locked by snap fitting through the annular base.

To this end, the pushing means are, for example, in the form of a tube which is adapted to be inserted in the guiding tube, preferably aligned with the manipulating shaft, said pushing tube having a dock at one end for receiving the annular base of the staple.

Thus, the staple and the pushing tube are intended to be inserted into the guiding tube and the pushing means can be used to push the staple right into the guide jaws, enabling said staple, when they clamp the gastric wall, to pass through the gastric wall and form a loop in order to come to be locked through the annular base.

Advantageously, the assembly comprises means for pulling the looped end of the staple for clamping it and securely fixing it.

As an example, the pulling means comprise a pulling shaft inserted in the pushing tube and having an end lug intended to engage with the notched shaft in order to be able to pull on the end of said staple to tighten the loop.

Preferably, the pulling shaft is connected to a handle which can be actuated against elastic restoring means in order to produce a pull on the pulling shaft.

Advantageously, the device comprises a member for cutting the end of the staple, pivotably mounted inside the pushing tube, in order to pass from a rest position to a cutting position, and a cam connected to a handle which can be actuated in order to pull on the cam, the cam being displaceable in order to force the cutting member to move into its cutting position.

The endoscopic device is guided, for example, by an endoscope comprising a viewing head fixed to guiding means.

BRIEF DESCRIPTION OF THE DRAWINGS

Other advantages and features will become more apparent from the following description of a preferred embodiment of the invention, given by way of non-limiting example and with reference to the accompanying figures, in which.

DETAILED DESCRIPTION OF THE INVENTION

Figure 1:
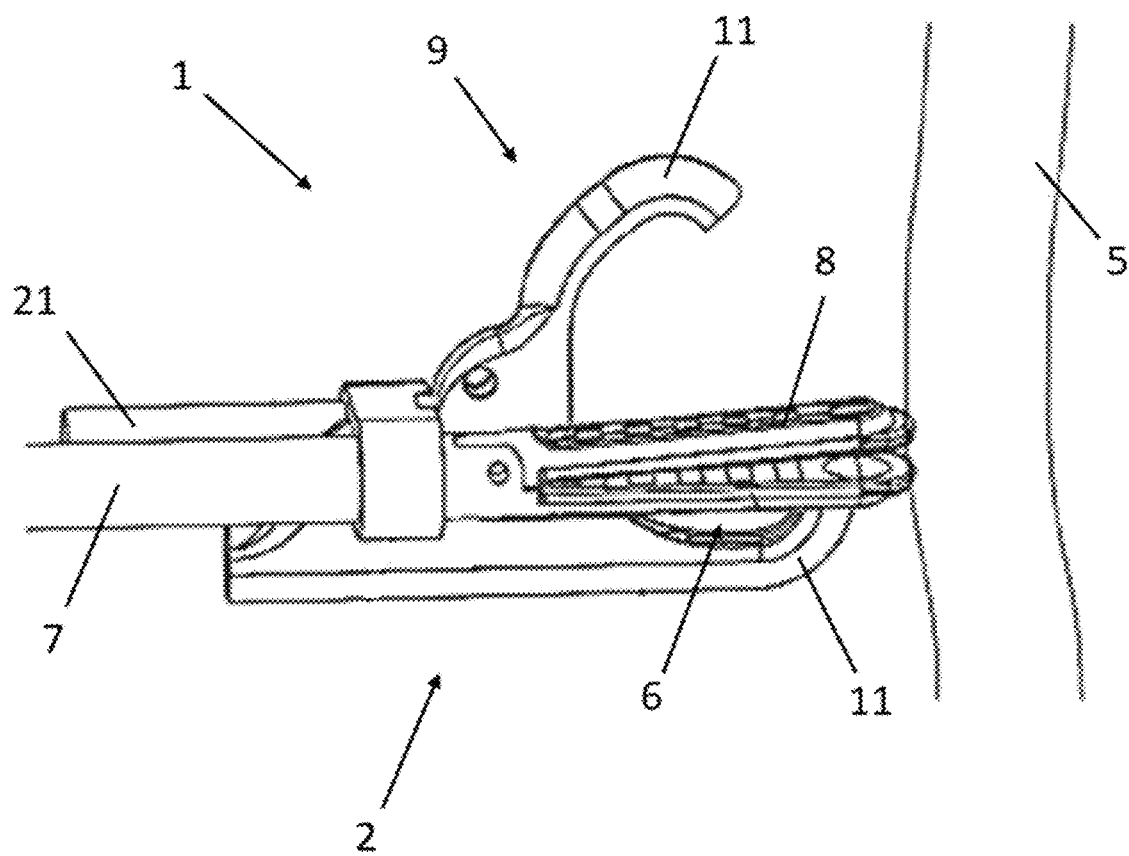
FIG. 1 is a diagrammatic perspective representation illustrating the guiding means for the staple, in the form of jaws, and grasping/pulling means in the form of a clamp, close to a gastric wall.

With reference to FIGS. 1 to 13, the invention concerns an endoscopic gastric plication device (1) used for the treatment of obesity. The device (1) is in particular intended to come to clamp a portion of the internal wall of the stomach and of pulling on it in order to form a fold and fix a staple around said fold. Successive similar operations can position a plurality of staples in order to reduce the stomach volume and combat obesity.

To this end, the device (1) in accordance with the invention is intended to be used endoscopically and therefore to be inserted into a stomach via the esophagus. The device (1) comprises an assembly (2) which is capable of cooperating, in a manner which is known for this type of device (1) which is used endoscopically, with control means (23) in order to actuate the assembly (2).

Under the action of the control means (23), the assembly (2) of the device (1) can therefore be used to position and fix a staple (3) around a fold (4) formed in a gastric wall (5).

To this end, the assembly (2) comprises means (6) for grasping/pulling a portion of the gastric wall (5) arranged at the end of a manipulating shaft (7) intended to be connected to the control means (23) and which can be actuated by said control means (23) in order to come into engagement with the gastric wall (5) and pull on it in order to form the fold (4).

These grasping/pulling means (6) may be of any appropriate type such as, for example, in the form of a helical needle intended to be planted in the gastric wall (5), or in fact in the form of a vacuum system, but preferably, the grasping/pulling means (6) are in the form of an articulated clamp (8).

In this manner, once inserted into the stomach, by actuating the control means (23), a surgeon can manipulate the clamp (8) in order to come to clamp the gastric wall (5) and form a fold (4) by pulling on the clamp (8).

The clamp (8) comprises, for example, a fixed jaw and an articulated jaw, for example against an elastic restoring member which tends to urge the articulated jaw against the fixed jaw in a clamping position. The articulation of the article jaw may, for example, be produced by pulling on a cable fixed on the one hand to the articulated jaw and on the other hand connected to the control means (23) by passing inside the manipulating shaft (7), for example. The jaws of the grasping/pulling means (6) are flat, for example, and have a notched contact surface in order to grab the gastric wall (5) in an optimal manner.

The assembly (2) of the device (1) in accordance with the invention also comprises means (9) for guiding a staple (3) around a fold (4) of the gastric wall (5). These guiding means (9) are intended to guide a staple (3), pushed through them, so that said staple (3) makes a loop around the fold (4) of the gastric wall (5).

To this end, the guiding means (9) comprise, for example, a guiding tube (10) opening onto two jaws (11) having sections in the form of troughs, in particular open facing one another, for the passage of and for guiding the staple (3). Under the action of the control means (23), the jaws (11) are capable of passing from a closed guiding position in which the jaws (11) clamp the fold (4) of the gastric wall (5) and come to face each other in order to form a path for the staple (3), to an open position for releasing the staple (3).

Figure 11:
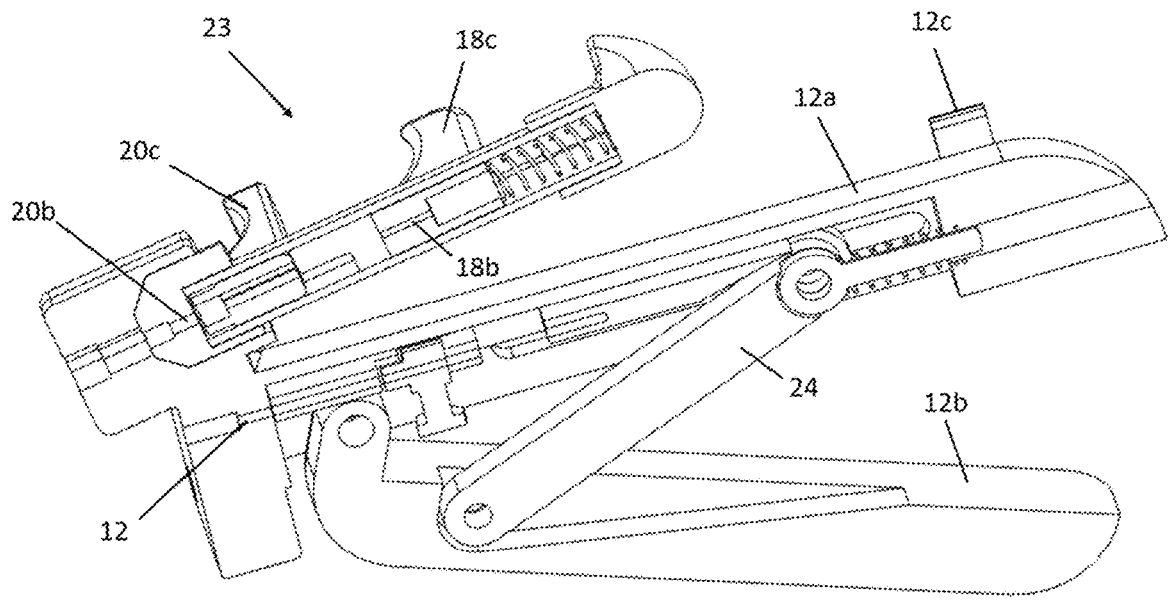
FIG. 11 is a representation illustrating the control means, viewed in perspective and in section.
Figure 12:
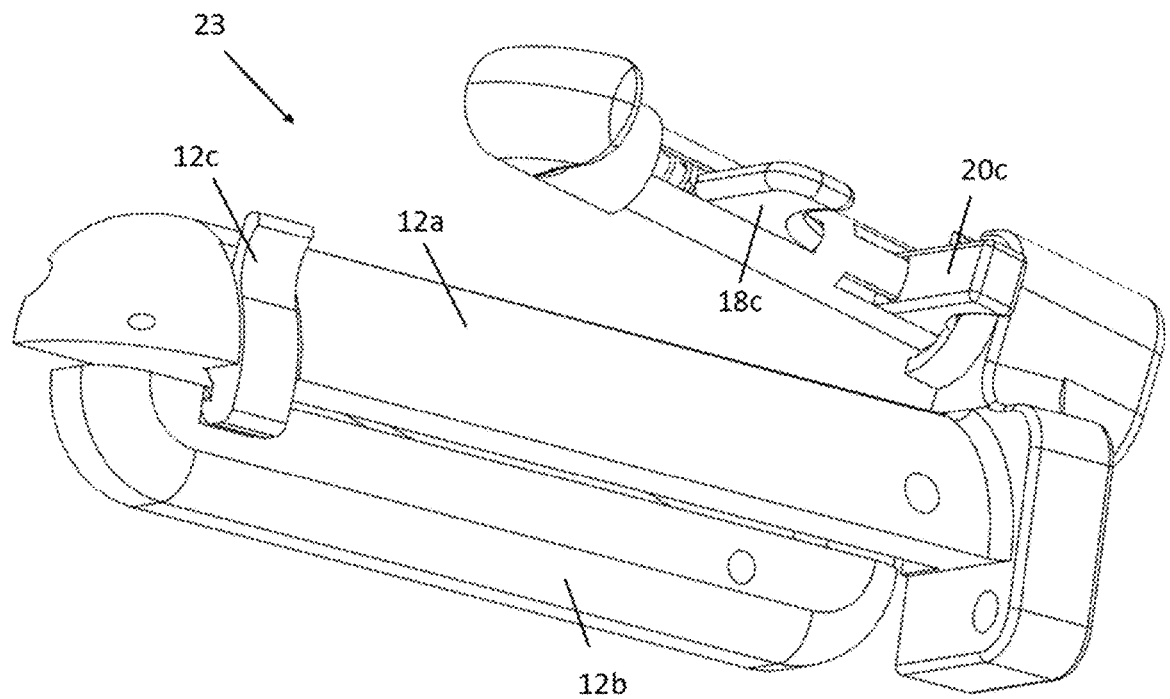
FIG. 12 is a representation which is similar to that of FIG. 11, viewed from an opposite side.
Figure 13:
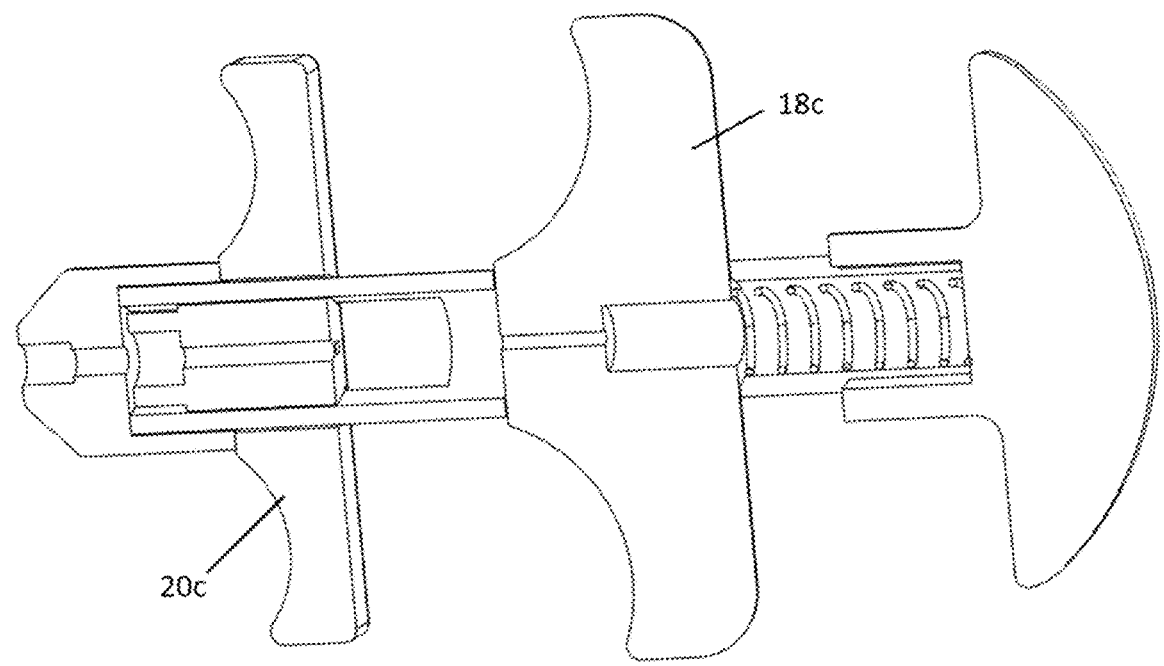
FIG. 13 is a representation illustrating the control handle of the pulling shaft and the cutting member.

The jaws (11) of the guiding means (9) are articulated in any appropriate manner, and preferably in the same manner as the jaws of the clamp (8). As an example, one of the jaws (11) of the guiding means (9) is fixed, while the other is articulated by means of a cable (12). Referring now to FIGS. 11 and 12, the cable (12) is, for example, connected to the control means (23), which comprise two portions (12a, 12b) which are pivotably mounted with respect to each other between an open position, FIG. 11, corresponding to a position which does not pull on the cable (12) and with the jaws (11) in an open position, to a closed position, FIG. 12, corresponding to a position which pulls on the cable (12) and the jaws (11) are closed. The closed position is, for example, locked by at least one catch (12c) mounted on one of the portions (12a, 12b) and coming into engagement in the other portion (12b, 12a).

The cable (12) is, for example, pulled by a crank system (24) comprising a first end which is pivotably mounted on one of the portions (12b), while the second end is pivotably and slidably mounted against a spring inside the other portion (12a). Said second end is attached to the cable (12) in order to exert a pull when the two portions (12a, 12b) are brought towards each other.

Figure 8:
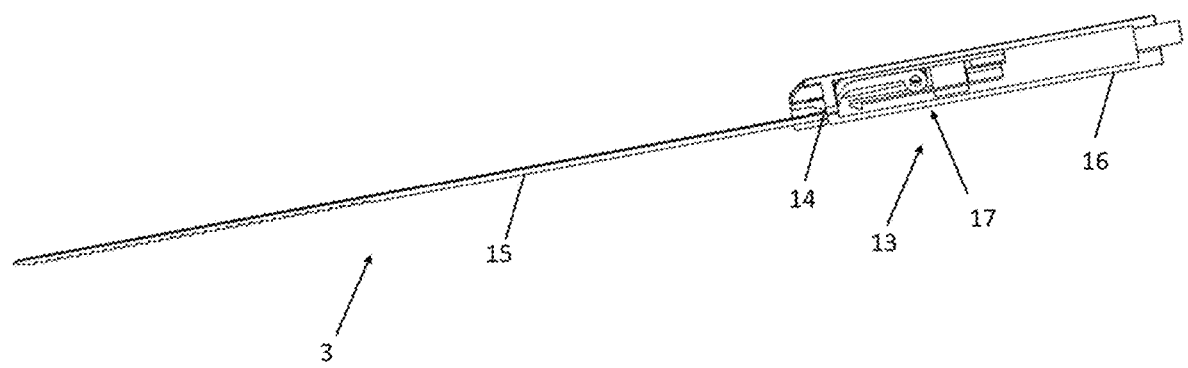
FIG. 8 is a diagrammatic representation illustrating a staple and, in section, the means for pushing, pulling and cutting the staple.
Figure 9:
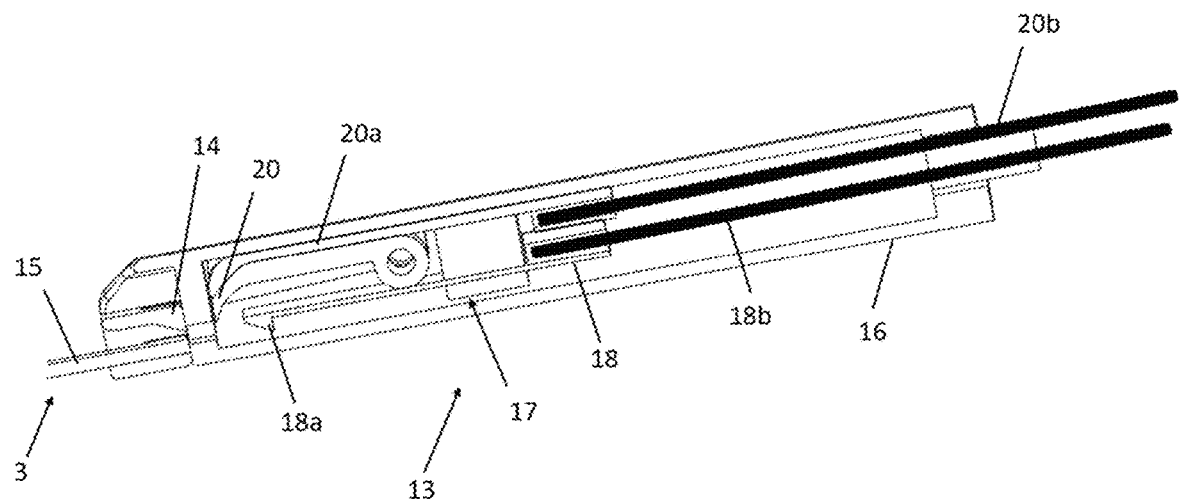
FIG. 9 is a detailed sectional representation of the means for pushing, pulling and cutting the staple.
Figure 10:
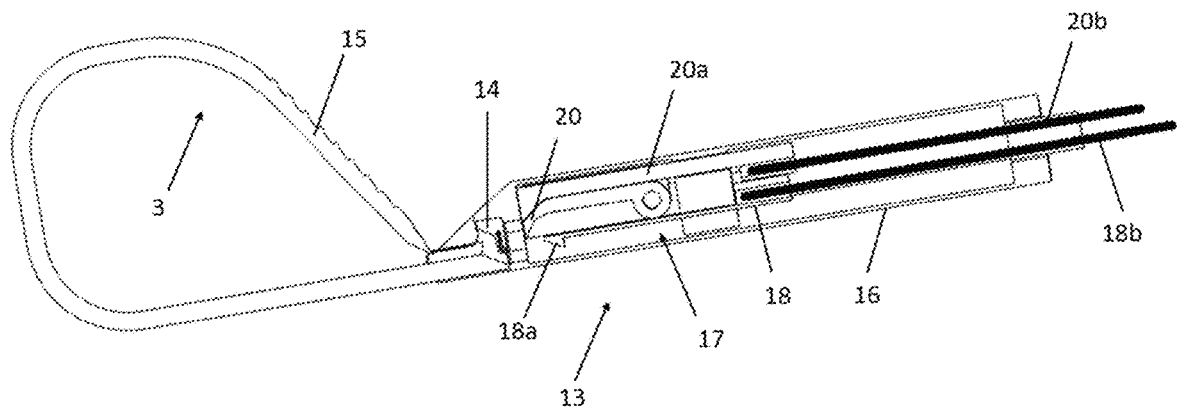
FIG. 10 is a representation which is similar to that of FIG. 9, in which the staple has been pushed in order to form a loop.

With reference to FIGS. 8 to 10, the assembly (2) of the plication device (1) in accordance with the invention also comprises a staple (3) and means (13) for pushing said staple (3) in the guiding means (9), said staple (3) being intended to come to pass through the fold (4) of the gastric wall (5) and make a loop around it, while being guided by the guiding means (9).

The staple (3) may have any appropriate shape and comprises an annular base (14) from which a notched shaft (15) extends which is intended to be looped and come to be inserted and locked by snap fitting through the annular base (14).

The means (13) for pushing the staple (3) may, for example, be in the form of a pushing tube (16) which is adapted for insertion into the guiding tube (10). This pushing tube (16) has a dock for receiving the annular base (14) of the staple (3) at one end.

Thus, the staple (3) may be positioned at the end of the pushing tube (16) and in the extension thereof. The staple (3) and the pushing tube (16) are intended to be inserted into the guiding tube (10) and, by pushing on the pushing tube (16), this can guide the staple (3) in the guiding means (9), the jaws (11) of which form a kind of ramp in the closed position in order to make the staple loop in a manner such that the free end of the staple (3) will be inserted into and locked by snap fitting through the annular base (14), in particular penetrating into the interior of the pushing tube (16).

In order to tighten the loop formed by the staple (3), the assembly (2) of the device (1) in accordance with the invention comprises means (17) for pulling the looped end of the staple (3).

As an example, the pulling means (17) comprise a pulling shaft (18) inserted into the pushing tube (16) and having an end lug (18a) intended to be engaged with the notched shaft (15) in order to pull on the end of the staple (3) and tighten the loop. Pulling is, for example, carried out by means of a cable (18b) connected to a handle (18c) which optionally comprises control means (23) which can be actuated against elastic restoring means such as a spring, see FIG. 11.

Once tightened, the free and looped end of the staple (3) needs to be cut so that it does not compromise or injure the inside of the stomach. To this end, the pushing tube (16) comprises a member (20) for cutting the end of the staple (3), pivotably mounted inside the pushing tube (16), in order to pass from a rest position to a cutting position.

The pushing tube (16) comprises a cam (20a) which is connected, for example via a cable (20b), to a handle (20c) which optionally comprises control means (23), which can be actuated in order to pull on the cam (20b), the cam being displaceable in order to force the passage of the cutting member (20) into the cutting position.

In order to guide the device (1) in accordance with the invention inside the stomach of a patient, the assembly (2) comprises an endoscope comprising a viewing head (21) fixed to guiding means (9). As an example, and referring now to FIG. 6, the guiding means (9) comprise a base plate (22) having a bore (22a) for the passage of the endoscope (21), a bore (22b) for the passage of the clamp (8), a bore (22c) for the passage of the cable (12) for closing the jaws (11), a bore (22d) for the passage of the staple (3), and a pushing tube (16).

The method for using the gastric plication device (1) in accordance with the invention will now be described.

The device (1) is inserted into the esophagus of a patient until it passes into the stomach.

The grasping/pulling means (6) and the guiding means (9) are in the open position and the device is brought towards the gastric wall (5) until it comes into contact.

With reference to FIG. 1, the clamp (8) of the grasping/pulling means (6) is closed in order to capture a portion of the gastric wall (5) and is pulled backwards to form a fold (4).

Figure 2:
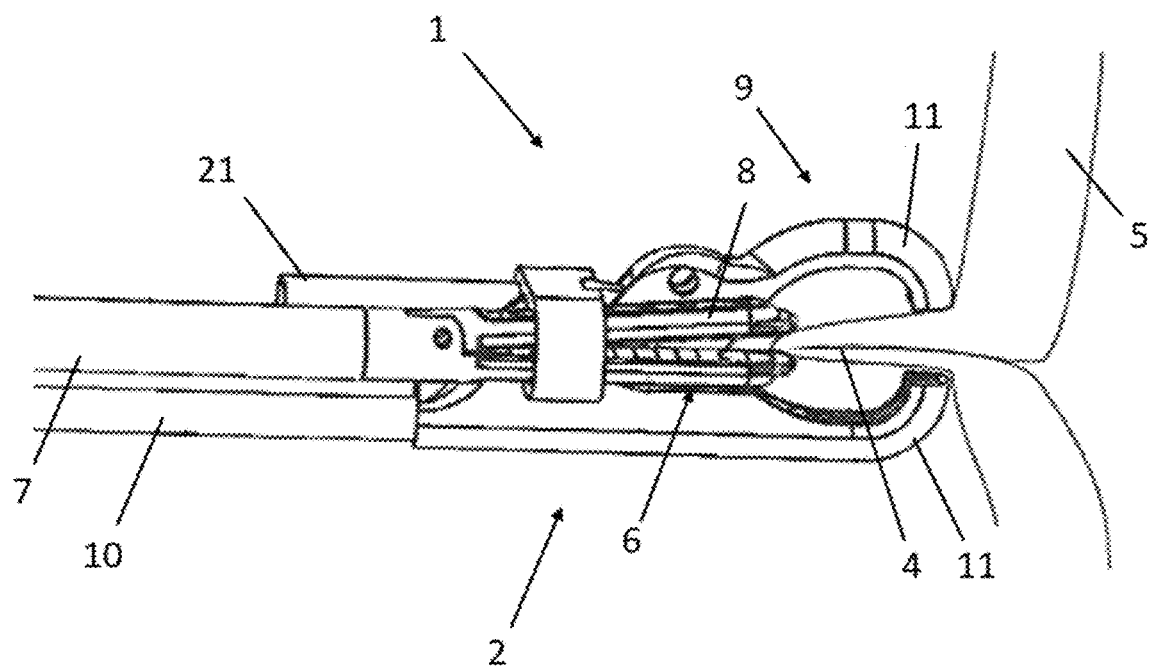
FIG. 2 is a diagrammatic representation similar to that of FIG. 1, with the grasping/pulling means having been pulled backwards in order to form a fold of the gastric wall, and the jaws being represented in a closed guiding position in which they clamp the fold of the gastric wall.

With reference to FIG. 2, the jaws (11) of the guiding means (9) are closed in order to clamp the fold (4) of the gastric wall (5).

Figure 3:
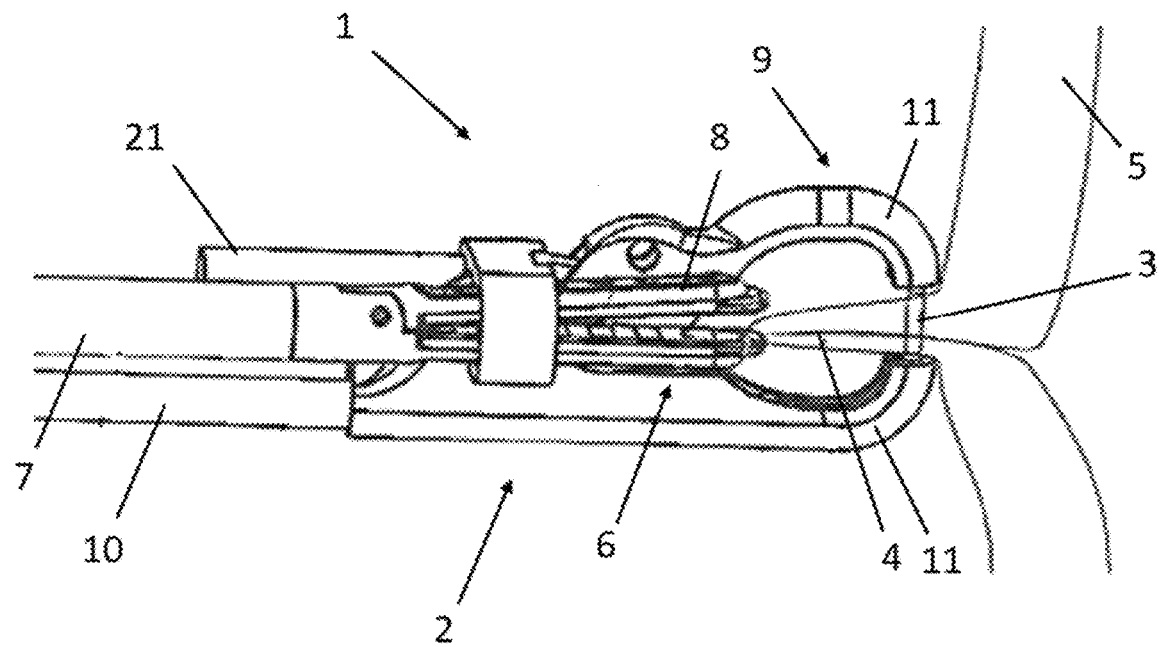
FIG. 3 is a representation similar to that of FIG. 2, with a staple having been pushed towards the guide jaw in order to pass through and form a loop around the fold of the gastric wall.

With reference to FIG. 3, a staple (3) inserted in the guiding tube (10) is pushed towards said guiding means (9) via the pushing tube (16).

The staple (3), guided by the trough or channel shape of the jaws (11) of the guiding means (9), pierces and passes through the gastric fold (4) and will form a loop until the free end of the staple (3) engages inside the annular base (14) of the staple (3) and inserts itself inside the pushing tube (16).

The insertion of the free end of the staple (3) into the annular base (14) enables the notches of said staple (3) to lock by snap fitting with the annular base (14) of the staple (3) and with the lug (18a) of the pulling shaft (18).

Next, the free end of the staple (3) inserted inside the pushing tube (16) and engaged with the lug (18a) of the pulling shaft (18) is tightened by pulling on said pulling shaft (18). Next, the superfluous portion of the staple (3) is cut by pulling on the cam (20a) in order to pivot the cutting member (20).

Figure 4:
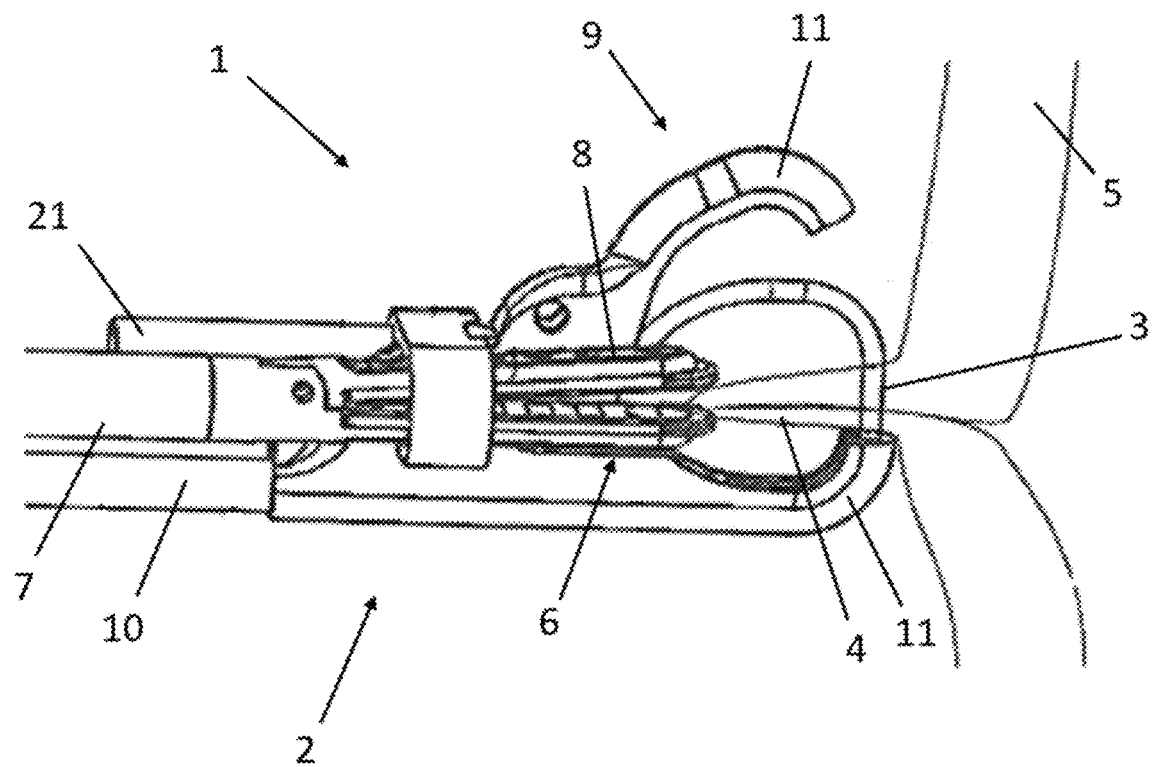
FIG. 4 is a representation similar to that of FIG. 3, in which the jaws of the guiding means have been shown in the open position for releasing the staple.

Next, with reference to FIG. 4, the jaws (11) of the guiding means (9) are returned to the open release position. In fact, in this position, the jaws (11) of the guiding means (9) may be drawn back, releasing the staple (3).

Figure 5:
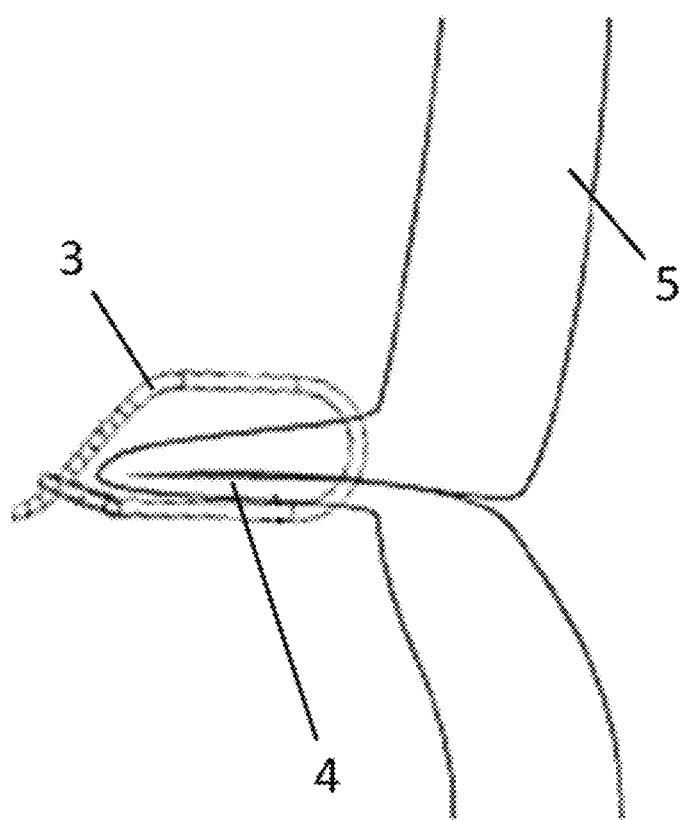
FIG. 5 illustrates the staple alone, looped and locked around the fold of the gastric wall.
Figure 6:
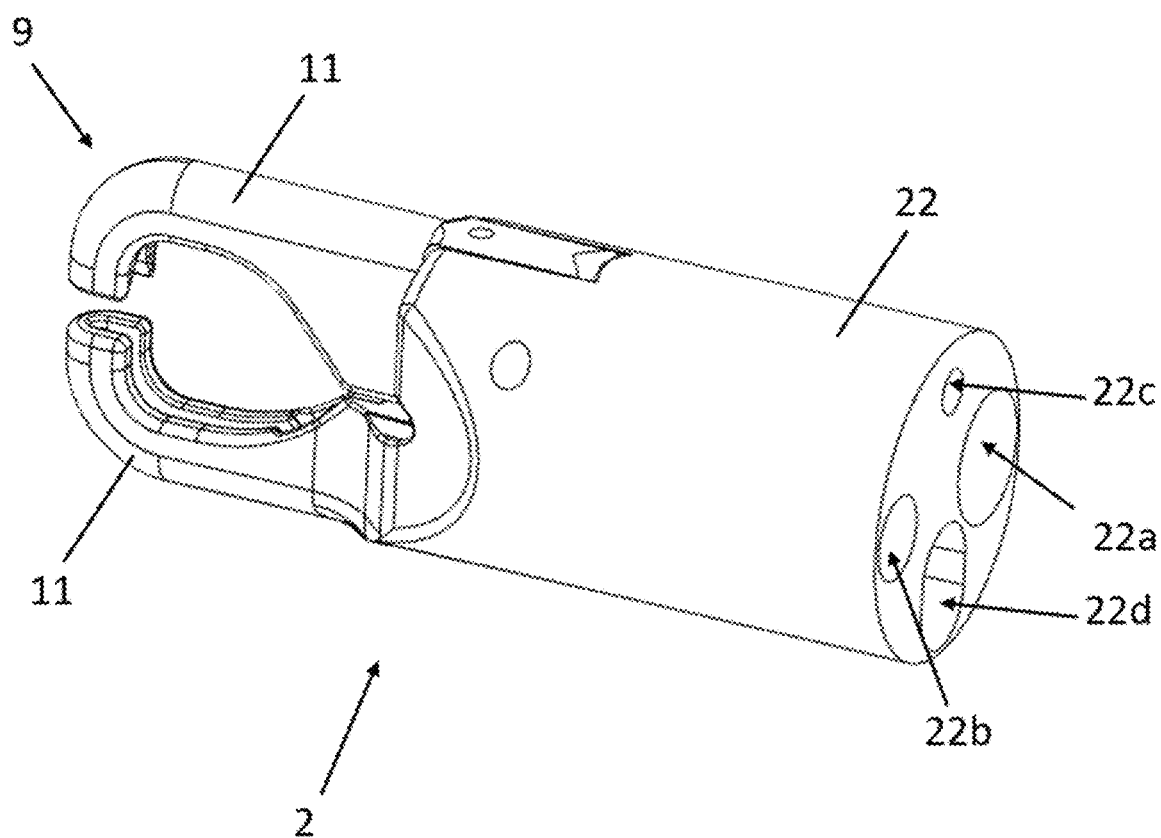
FIG. 6 shows a perspective view of the guiding means in the form of jaws, in the closed position.
Figure 7:
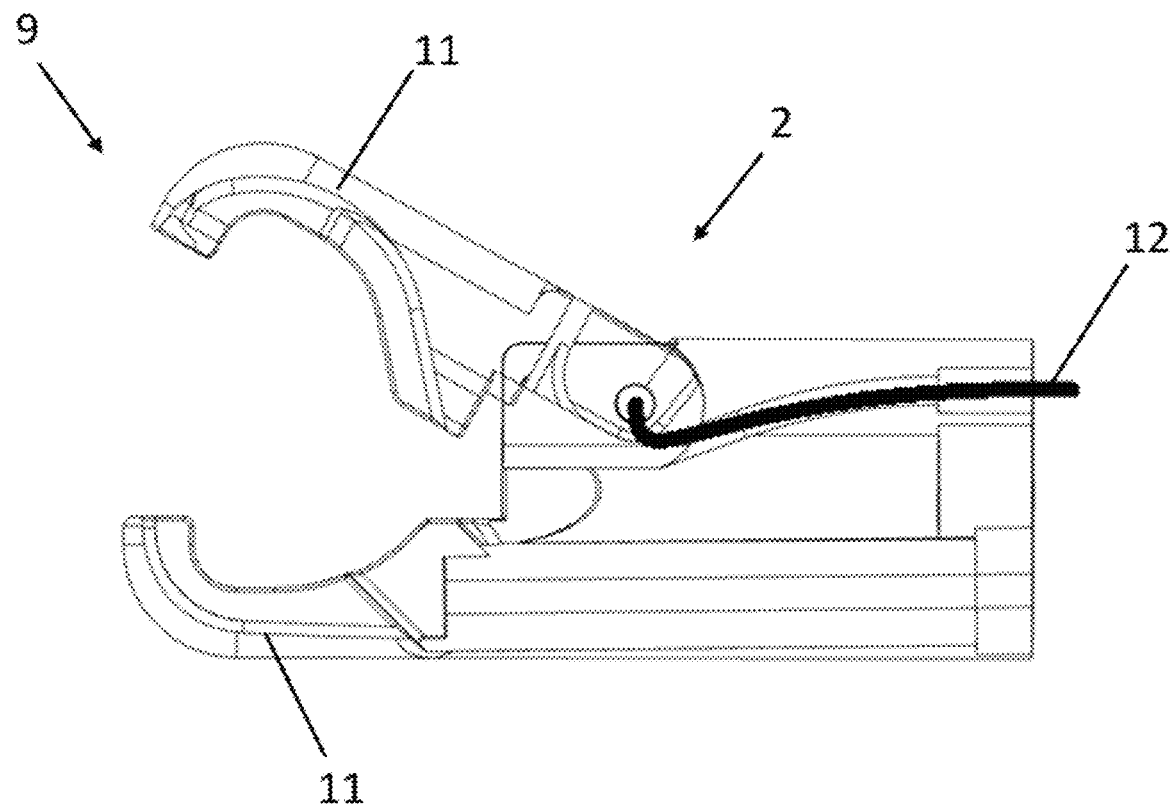
FIG. 7 is a representation similar to that of FIG. 6, illustrating, in section, the guiding means in the open position.

The clamp (8) of the grasping/pulling means (6) is also open, in order to permit the withdrawal of the device (1) and to leave the staple (3) in place, see FIG. 5.

These successive steps are carried out as many times as is necessary to position a plurality of staples (3) around folds (4) formed on the inside of the gastric wall (5) in order to reduce the volume of the stomach and combat obesity.

The invention claimed is:

1. An endoscopic gastric plication device comprising an assembly for positioning and fixing a staple around a fold of a gastric wall, characterized in that said device comprises:
   a mechanism for grasping/pulling a portion of a gastric wall arranged at the end of a manipulating shaft and which can be actuated to engage the gastric wall and pull on it to form a fold;
   a mechanism for guiding a staple around the fold of the gastric wall;
   at least one staple, and a mechanism for pushing the staple in the guiding mechanism, such that the staple passes through and makes a loop around the fold, guided by the guiding mechanism; and
   a mechanism for pulling the looped end of the staple.

2. The device as claimed in claim 1, characterized in that the grasping/pulling mechanism is in the form of a clamp.

3. The device as claimed in claim 1, characterized in that the grasping/pulling mechanism is in the form of a helical needle extending in the extension of the manipulating shaft.

4. The device as claimed in claim 1, characterized in that the grasping/pulling mechanism is in the form of a vacuum system.

5. The device as claimed in claim 1, characterized in that the guiding mechanism comprises a guiding tube opening onto two articulated jaws having sections in the form of a trough for passing the staple through and guiding the staple, the jaws being capable of moving from a closed guiding position in which the jaws clamp the fold of the gastric wall, to an open position for releasing the staple.

6. The device as claimed in claim 1, characterized in that the staple comprises an annular base and a notched shaft, the notched shaft being configured to be looped and to be inserted into and locked by snap fitting through the annular base.

7. The device as claimed in claim 5, characterized in that the pushing mechanism is in the form of a pushing tube which is adapted to be inserted in the guiding tube and has a dock at one end for receiving the annular base of the staple.

8. The device as claimed in claim 7, characterized in that the pulling mechanism comprises a pulling shaft inserted in the pushing tube, the pulling shaft having an end lug) that engages with the notched shaft to be able to pull on the end of the staple to tighten the loop.

9. The device as claimed in claim 7, characterized in that the pulling shaft is connected to a handle which can be actuated against an elastic restoring mechanism to produce a pull on the pulling shaft.

10. The device as claimed in claim 7, further comprising a member for cutting the end of the staple, pivotably mounted inside the pushing tube to pass from a rest position to a cutting position, and a cam connected to a handle which can be actuated to pull on the cam, the cam being displaceable to force the cutting member to move into its cutting position.

11. The device as claimed in claim 1, characterized in that the device comprises an endoscope comprising a viewing head fixed to the guiding mechanism.

\* \* \* \* \*